US00PP19496P2

(12) United States Plant Patent
Bunker

(10) Patent No.: US PP19,496 P2
(45) Date of Patent: Nov. 25, 2008

(54) ***GAURA* PLANT NAMED 'STAR PINK'**

(50) Latin Name: ***Gaura lindheimeri*×*Gaura coccinea***
Varietal Denomination: Star Pink

(76) Inventor: Edward Bunker, P.O. Box 7354, Redland Bay, Queensland 4165 (AU)

( * ) Notice: Subject to any disclaimer, the term of this patent is extended or adjusted under 35 U.S.C. 154(b) by 0 days.

(21) Appl. No.: 11/978,508

(22) Filed: Oct. 29, 2007

(51) Int. Cl.
*A01H 5/00* (2006.01)

(52) U.S. Cl. ..... Plt./432
(58) Field of Classification Search ..... Plt./432
See application file for complete search history.

(56) References Cited

PUBLICATIONS

GTITM UPOVROM Citation for 'Star Pink' as per CA PBR 06–5476; May 10, 2006.*

* cited by examiner

*Primary Examiner*—Kent L Bell
(74) *Attorney, Agent, or Firm*—C. A. Whealy

(57) ABSTRACT

A new and distinct cultivar of *Gaura* plant named 'Star Pink', characterized by its compact and upright growth habit; freely branching habit; freely flowering habit; dark pink-colored flowers that are held above the foliage on strong peduncles; long flowering period; and good garden performance.

1 Drawing Sheet

Botanical designation: *Gaura lindheimeri*×*Gaura coccinea.*
Cultivar denomination: 'Star Pink'.

BACKGROUND OF THE INVENTION

The present invention relates to a new and distinct cultivar of *Gaura,* botanically known as *Gaura lindheimeri*×*Gaura coccinea* and hereinafter referred to by the name 'Star Pink'.

The new *Gaura* is a product of a planned breeding program conducted by the Inventor in Redland Bay, Queensland, Australia. The objective of the breeding program is to create new compact *Gaura* cultivars that flower for a long period of time.

The new *Gaura* originated from a cross-pollination made by the Inventor in December, 2002 in Redland Bay, Queensland, Australia of a proprietary selection of *Gaura lindheimeri*×*Gaura coccinea* identified as code number 99-003, not patented, as the female, or seed, parent with a proprietary selection of *Gaura lindheimeri*×*Gaura coccinea* identified as code number 99-017, not patented, as the male, or pollen, parent. The new *Gaura* was discovered and selected by the Inventor as a single flowering plant within the progeny of the stated cross-pollination in a controlled environment in Redland Bay, Queensland, Australia.

Asexual reproduction of the new *Gaura* by terminal cuttings in a controlled environment in Redland Bay, Queensland, Australia since September, 2003, has shown that the unique features of this new *Gaura* are stable and reproduced true to type in successive generations.

SUMMARY OF THE INVENTION

The cultivar Star Pink has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Star Pink'. These characteristics in combination distinguish 'Star Pink' as a new and distinct cultivar of *Gaura:*

1. Compact and upright growth habit.
2. Freely branching habit.
3. Freely flowering habit.
4. Dark pink-colored flowers that are held above the foliage on strong peduncles.
5. Long flowering period.
6. Good garden performance.

Plants of the new *Gaura* can be compared to plants of the female parent selection. Plants of the new *Gaura* differ from plants of the female parent selection in the following characteristics:

1. Plants of the new *Gaura* are more compact and denser than plants of the female parent selection.
2. Plants of the new *Gaura* have lighter colored leaves than plants of the female parent selection.
3. Plants of the new *Gaura* have larger flowers than plants of the female parent selection.
4. Plants of the new *Gaura* have stronger peduncles than plants of the female parent selection.

Plants of the new *Gaura* can be compared to plants of the male parent selection. Plants of the new *Gaura* differ from plants of the male parent selection in the following characteristics:

1. Plants of the new *Gaura* are more compact and denser than plants of the male parent selection.
2. Plants of the new *Gaura* and the male parent selection differ in flower color as plants of the male parent selection have red-colored flowers.

Plants of the new *Gaura* can also be compared to plants of the *Gaura* cultivar Perky Pink, disclosed in U.S. Plant Pat. No. 16,120. In side-by-side comparisons conducted by Bonsall, Calif., plants of the new *Gaura* differed from plants of the cultivar Perky Pink in the following characteristics:

1. Plants of the new *Gaura* were more upright than and not as outwardly spreading as plants of the cultivar Perky Pink.
2. Plants of the new *Gaura* had darker pink-colored flowers than plants of the cultivar Perky Pink.

BRIEF DESCRIPTION OF THE PHOTOGRAPHS

The accompanying colored photographs illustrate the overall appearance of the new *Gaura,* showing the colors as true as it is reasonably possible to obtain in colored reproductions of this type. Colors in the photographs may differ slightly from the color values cited in the detailed botanical description which accurately describe the colors of the new *Gaura.*

The photograph at the bottom of the sheet comprises a side perspective view of a typical plant of 'Star Pink' grown in a container.

The photograph at the top of the sheet is a close-up view of typical flowers of 'Star Pink'.

DETAILED BOTANICAL DESCRIPTION

The photograph and following observations, measurements and values describe plants grown in Bonsall, Calif. during the spring in an outdoor nursery and conditions which approximate commercial *Gaura* production. During the production of the plants, day temperatures ranging from 13° C. to 35° C. and night temperatures ranging from 7° C. to 18° C. Rooted young plants had been growing for about seven weeks when the photographs and description were taken. In the following description, color references are made to The Royal Horticultural Society Colour Chart, 1995 Edition, except where general terms of ordinary dictionary significance are used.

Botanical classification: *Gaura lindheimeri*×*Gaura coccinea* cultivar Star Pink.

Parentage:

*Female, or seed, parent.*—Proprietary selection of *Gaura lindheimeri*×*Gaura coccinea* identified as code number 99-003, not patented.

*Male, or pollen, parent.*—Proprietary selection of *Gaura lindheimeri*×*Gaura coccinea* identified as code number 99-017, not patented.

Propagation:

*Type.*—By vegetative cuttings.

*Time to initiate roots, summer.*—About two weeks.

*Time to initiate roots, winter.*—About three weeks.

*Time to produce a rooted young plant, summer.*—About four weeks.

*Time to produce a rooted young plant, winter.*—About six weeks.

*Root description.*—Fine, fibrous; white in color.

*Rooting habit.*—Freely branching; moderately dense.

Plant description:

*Plant and growth habit.*—Herbaceous perennial. Compact and upright growth habit. Freely branching habit with about eight to nine lateral branches developing per plant; dense and bushy habit. Moderately vigorous growth habit.

*Plant height.*—About 31 cm.

*Plant diameter.*—About 21 cm.

Lateral branch description:

*Length.*—About 28 cm.

*Diameter.*—About 3 mm.

*Internode length.*—About 1.5 cm.

*Aspect.*—Mostly upright.

*Texture, immature.*—Pubescent.

*Texture, mature.*—Glabrous.

*Color, immature.*—146A.

*Color, mature.*—183A.

Foliage description:

*Arrangement.*—Alternate; simple.

*Length.*—About 7.2 cm.

*Width.*—About 8 mm.

*Shape.*—Narrowly elliptic to lanceolate.

*Apex.*—Acute.

*Base.*—Attenuate.

*Margin.*—Entire; occasionally with a few irregular points.

*Texture, upper and lower surfaces.*—Smooth, glabrous.

*Venation pattern.*—Pinnate; arcuate.

*Color.*—Developing foliage, upper and lower surfaces: 147A. Fully expanded foliage, upper surface: 147A; venation, 185B. Fully expanded foliage, lower surface: 147B; venation, 182B to 182C.

*Petiole length.*—About 1.4 cm.

*Petiole diameter.*—About 2 mm.

*Petiole texture, upper and lower surfaces.*—Smooth, glabrous.

*Petiole color, upper surface.*—185B.

*Petiole color, lower surface.*—182C.

Flower description:

*Flower arrangement and habit.*—Single sessile flowers arranged on upright terminal spikes. Freely flowering habit with about 30 flowers per inflorescence. Flowers persistent. Flowers face initially upright then mostly outwardly.

*Fragrance.*—None detected.

*Natural flowering season.*—Plants flower continuously from April through October in Southern California. Early flowering habit, plants typically beginning flowering about four weeks after planting.

*Flower longevity.*—Individual flowers last about three days on the plant.

*Inflorescence height.*—About 14 cm to 15 cm.

*Inflorescence diameter.*—About 2.5 cm.

*Flower diameter.*—About 2.5 cm to 2.7 cm.

*Flower depth* (*height*).—About 1.8 cm.

*Flower bud.*—Shape: Narrowly oblanceolate. Length: About 1.7 cm. Diameter: About 2.5 mm. Color: 185A to 185B.

*Petals.*—Arrangement: Four in a single whorl. Length: About 1.3 cm to 1.6 cm. Width: About 7 mm. Shape: Roughly obovate. Apex: Obtuse. Base: Acute to attenuate. Margin: Entire. Texture, upper and lower surfaces: Smooth, glabrous; velvety. Color: When opening, upper surface: 75D. When opening, lower surface: 69B. Fully opened, upper and lower surfaces: 69C; venation, close to 75D.

*Sepals.*—Arrangement: Four in a single whorl fused at the base; calyx, elongated tubular. Length: About 1.5 cm. Width: About 1.5 mm. Shape: Narrowly lanceolate. Apex: Acute. Margin: Entire. Texture, upper surface: Smooth, glabrous. Texture, lower surface: Pubescent. Color, upper surface: 183B. Color, lower surface: 183A.

*Peduncles.*—Length: About 2.4 cm. Diameter: About 2 mm. Strength: Strong. Texture: Pubescent. Color: 187B.

*Reproductive organs.*—Stamens: Quantity: About eight per flower. Filament length: About 7 mm. Filament color: 75C. Anther shape: Lanceolate. Anther length: About 3 mm. Anther color: 59A. Pollen amount: Scarce. Pollen color: 4B. Pistils: Quantity: One per flower. Pistil length: About 2.2 cm. Style length: About 1.2 cm. Style color: 185C. Stigma shape: Four-parted. Stigma color: 157A. Ovary color: 59A. Seed/fruit: Seed and fruit development have not been observed on plants of the new *Gaura.*

Garden performance: Plants of the new *Gaura* have been observed to have good garden performance and tolerate wind, rain and temperatures ranging from about 1° C. to about 40° C.

Pathogen/pest resistance: Plants of the new *Gaura* have not been observed to be resistant to pathogens and pests common to *Gaura.*

It is claimed:

1. A new and distinct *Gaura* plant named 'Star Pink' as illustrated and described.

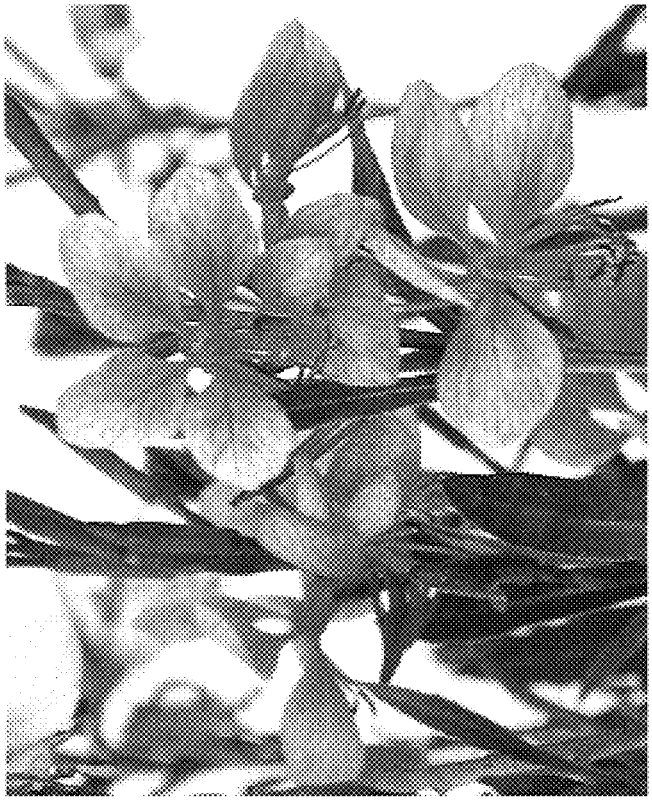
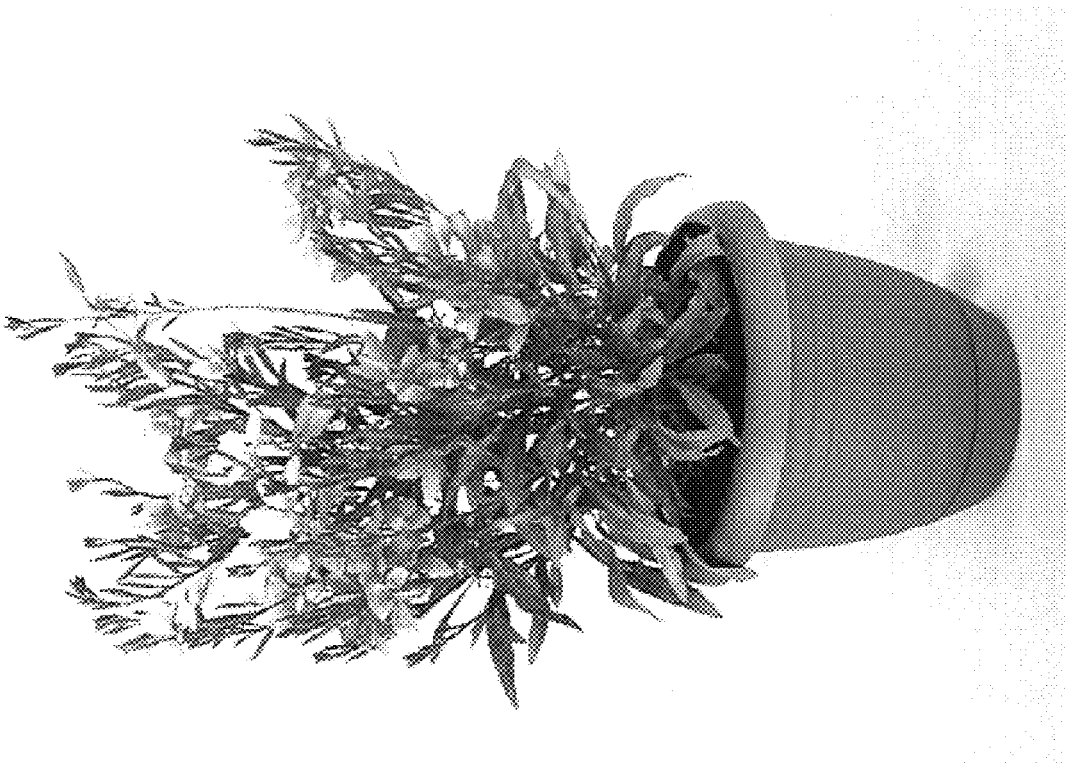

* * * * *